United States Patent
Haber et al.

(10) Patent No.: US 10,492,713 B2
(45) Date of Patent: Dec. 3, 2019

(54) SYSTEMS AND METHODS FOR MONITORING A DEPTH OF NEUROMUSCULAR BLOCKADE

(71) Applicant: THE CLEVELAND CLINIC FOUNDATION, Cleveland, OH (US)

(72) Inventors: Georges-Pascal Haber, Westlake, OH (US); Vishnuvardhan Ganesan, Harrisburg, PA (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 176 days.

(21) Appl. No.: 15/613,594

(22) Filed: Jun. 5, 2017

(65) Prior Publication Data

US 2017/0347921 A1   Dec. 7, 2017

Related U.S. Application Data (60) Provisional application No. 62/345,014, filed on Jun. 3, 2016.

(51) Int. Cl.
  *A61B 5/11*   (2006.01)
  *A61B 5/06*   (2006.01)
  (Continued)

(52) U.S. Cl.
  CPC ............ *A61B 5/1106* (2013.01); *A61B 5/062* (2013.01); *A61B 5/1108* (2013.01);
  (Continued)

(58) Field of Classification Search
  CPC ..... A61B 5/1106; A61B 5/1108; A61B 5/062; A61B 5/1126; A61B 5/6853;
  (Continued)

(56) References Cited

U.S. PATENT DOCUMENTS

| 4,157,087 A | * | 6/1979 | Miller | A61N 1/36003 600/554 |
| 4,214,593 A | * | 7/1980 | Imbruce | A61B 5/037 600/561 |

(Continued)

FOREIGN PATENT DOCUMENTS

WO   2014168952   10/2017

OTHER PUBLICATIONS

International Search Report corresponding to PCT/US2017/035902, dated Aug. 28, 2017, pp. 1-13.

*Primary Examiner* — Eric F Winakur
*Assistant Examiner* — Abid A Mustansir
(74) *Attorney, Agent, or Firm* — Tarolli, Sundheim, Covell & Tummino LLP (57) ABSTRACT

One aspect of the present disclosure relates to a system for monitoring a diaphragmatic twitch response. The diaphragmatic twitch response can be used to determine a depth of neuromuscular blockade. The system includes a neural stimulation device to stimulate a phrenic nerve of a subject, which has the effect of stimulating the subject's diaphragm. The system also includes a monitor to detect the diaphragm's response to the stimulation. For example, the monitor can include a nasogastric tube with two distally positioned inflatable balloons. Each of the inflatable balloons is coupled to a sensor to measure a corresponding pressure (e.g., an esophageal pressure and a gastric pressure). The pressure differential between the esophagus above the diaphragm and the stomach below the diaphragm (also referred to as the transdiaphragmatic pressure) can be used as a measure of the diaphragmatic twitch response.

19 Claims, 4 Drawing Sheets

(51) Int. Cl.
*A61B 5/00* (2006.01)
*A61N 1/05* (2006.01)
*A61N 1/36* (2006.01)
*A61B 34/20* (2016.01)

(52) U.S. Cl.
CPC .......... *A61B 5/1126* (2013.01); *A61B 5/6853* (2013.01); *A61B 5/6885* (2013.01); *A61N 1/0517* (2013.01); *A61N 1/36114* (2013.01); *A61B 5/1107* (2013.01); *A61B 2034/2051* (2016.02); *A61B 2562/0247* (2013.01)

(58) Field of Classification Search
CPC .......... A61B 5/6885; A61B 2562/0247; A61B 5/1107; A61B 2034/2051; A61N 1/36114; A61N 1/0517
See application file for complete search history.

(56) References Cited

U.S. PATENT DOCUMENTS

| | | | |
|---|---|---|---|
| 5,171,299 A * | 12/1992 | Heitzmann | A61M 25/104 604/100.03 |
| 6,454,728 B1 | 9/2002 | Tung | |
| 9,242,088 B2 | 1/2016 | Thakkar et al. | |
| 2003/0074039 A1* | 4/2003 | Puskas | A61N 1/0517 607/118 |
| 2005/0038484 A1 | 2/2005 | Knudson et al. | |
| 2008/0154191 A1* | 6/2008 | Gobel | A61B 5/037 604/101.05 |
| 2010/0094376 A1 | 4/2010 | Penner | |
| 2011/0046432 A1 | 2/2011 | Simon et al. | |
| 2012/0245482 A1 | 9/2012 | Bolser et al. | |
| 2013/0030497 A1* | 1/2013 | Karamanoglu | A61B 5/686 607/42 |
| 2014/0012157 A1 | 1/2014 | Gilhuly | |
| 2016/0058613 A1* | 3/2016 | Palazzolo | A61N 2/006 607/105 |

* cited by examiner

SYSTEMS AND METHODS FOR MONITORING A DEPTH OF NEUROMUSCULAR BLOCKADE

RELATED APPLICATIONS

This application claims the benefit of U.S. Provisional Application No. 62/345,014, filed Jun. 3, 2016, entitled "MONITORING NEUROMUSCULAR BLOCKADE USING DIAPHRAGAMATIC TWITCH." This provisional application is hereby incorporated by reference in its entirety for all purposes.

TECHNICAL FIELD

The present disclosure relates generally to measuring the depth of neuromuscular blockade and, more specifically, to systems and methods for monitoring a twitch response of a subject's diaphragm to measure the depth of neuromuscular blockade.

BACKGROUND

During certain surgeries, anesthesiologists administer neuromuscular blocking agents to paralyze patients while anesthetized. This paralysis is due to neuromuscular blockade, which must be monitored during the surgery. Current techniques for monitoring the neuromuscular blockade are based on a muscle twitch response a stimulation of a peripheral nerve. For example, a peripheral nerve (e.g., the ulnar nerve, facial nerve, or posterior tibial nerve) can receive a train of four stimulation, a double burst stimulation, or a tetanus stimulation and the associated muscle twitch response can be monitored. While monitoring the twitch response due to stimulation of the ulnar nerve, the facial nerve, or the posterior tibial nerve is simple and convenient for the anesthesiologists, the muscles providing the twitch response are not a reliable measure of the strength of the neuromuscular blockade, which can lead to the patient cycling in and out of acceptable levels of neuromuscular blockade.

The diaphragm, being one of the first muscles to recover from neuromuscular blockade, is relatively resistant to neuromuscular blockade. The twitch response of the diaphragm may provide a better reflection of the degree of neuromuscular blockade that is more accurate than the traditional twitch response due to stimulation of the ulnar nerve, the facial nerve, or the posterior tibial nerve. However, the twitch response of the diaphragm is neither simple nor convenient for anesthesiologists to monitor.

SUMMARY

The present disclosure relates generally to measuring the depth of neuromuscular blockade and, more specifically, to systems and methods for monitoring a twitch response of a subject's diaphragm to measure the depth of neuromuscular blockade.

In one aspect, the present disclosure can include a system that monitors a diaphragmatic twitch response to measure the depth of neuromuscular blockade. The system includes a neural stimulation device to stimulate a phrenic nerve of a subject. Stimulating the phrenic nerve has the effect of stimulating the subject's diaphragm. The system also includes a monitor to detect the diaphragm's twitch response to the stimulation. For example, the monitor can include a nasogastric tube comprising two inflatable balloons positioned in a distal portion of the nasogastric tube, each coupled to a sensor to measure a corresponding pressure (e.g., an esophageal pressure and a stomach, or gastric, pressure based on a positions of the two inflatable balloons). The pressure differential between the esophagus and the stomach (also referred to as the transdiaphragmatic pressure) can be used as a measure of diaphragmatic twitch response, which can indicate the depth of neuromuscular blockade.

In another aspect, the present disclosure can include a method for monitoring a diaphragmatic twitch response to measure the depth of neuromuscular blockade. The method can include placing equipment on a subject pre-operatively. The equipment includes a neural stimulation device and a monitoring device. The monitoring device can include two inflatable balloons positioned on a distal portion of a nasogastric tube; and a sensor attached to each inflatable balloon to measure an associated pressure when the inflatable balloons are inflated. The method also includes stimulating, with the stimulation device, the phrenic nerve of the subject with a series of pulses; and recording, with the recording device, a pressure differential between the esophagus of the subject and the stomach of the subject. The pressure differential is calculated based on pressure recordings by each of the sensors upon inflation of the inflatable balloons. The pressure differential corresponds to the diaphragmatic twitch based on the series of pulses stimulating the phrenic nerve. Based on the pressure differential, a status of a neuromuscular blockade can be determined.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Unless otherwise defined, all technical terms used herein have the same meaning as commonly understood by one of ordinary skill in the art to which the present disclosure pertains.

In the context of the present disclosure, the singular forms "a," "an" and "the" can also include the plural forms, unless the context clearly indicates otherwise.

The terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "neuromuscular blockade" can refer to the inhibition of neural transmission at the neuromuscular junction by administration of one or more neuromuscular blocking agents. The inhibition of neural transmission can cause paralysis of the subject's skeletal muscles, but not the smooth muscles. Neuromuscular blockade is used, for example, during surgery with anesthesia so that the patient is paralyzed while sleeping.

As used herein, the term "neuromuscular junction" can refer to a chemical synapse formed by the contact between a motor neuron and a muscle fiber. At the neuromuscular junction, the motor neuron can transmit a signal to the muscle fiber, which causes a muscle contraction.

As used herein, the term "paralysis" can refer to the loss of the ability to move one or more skeletal muscles. The paralysis seen with neuromuscular blockade is temporary and reversible.

As used herein, the term "twitch response" can relate to a brief, contractile response of a skeletal muscle elicited by stimulation of a neuron supplying the skeletal muscle.

As used herein, the term "nasogastric tube" can refer to a tube (often made of a biocompatible plastic) that is inserted into the nose or mouth, through the esophagus, and into the stomach.

As used herein, the term "inflatable balloon" can refer to a piece of expandable material that can be expanded from an initial geometry to an expanded geometry. The expansion can be triggered by the addition of air or a fluid (e.g., water, oil, saline, or the like).

As used herein, the terms "sensor" and "transducer" can be used interchangeably herein to refer to a device that detects or measures a physical property and records, indicates, or otherwise responds to the physical property. As an example, the sensor can be an electromyogram (EMG) electrode. As another example, the sensor can be a pressure sensor. In another example, the sensor can detect the acceleration of a contracting muscle.

As used herein, the term "neural prosthesis device" can refer to one or more devices that can stimulate a nerve. The nerve can be stimulated by electrical stimulation or magnetic stimulation. For example, the neural prosthesis device can include at least a pulse generator (e.g., an electric pulse generator, a magnetic pulse generator, or the like) that provides the timing and control of the stimulus and an application means (e.g., electrode, magnetic coil, or the like) that applies the stimulus to the nerve.

As used herein, the term "electrical stimulation" can refer to applying an electrical current to a nerve through an electrode. In some instances, the electrical stimulation can be non-invasive, with the electric current being delivered to the subject via one or more skin electrodes. In other instances, the electrical stimulation can be at least partially invasive, with the electric current being delivered to the subject via an internal electrode.

As used herein, the term "magnetic stimulation" can refer to the application of a magnetic field to a subject to stimulate a nerve. One type of magnetic stimulation is transcutaneous magnetic stimulation (tMS), in which a magnetic field is delivered to the subject by an external coil non-invasively.

As used herein, the terms "subject" and "patient" can be used interchangeably and refer to any warm-blooded organism including, but not limited to, a human being, a pig, a rat, a mouse, a dog, a cat, a goat, a sheep, a horse, a monkey, an ape, a rabbit, a cow, etc.

As used herein, the term "distal" can refer to a portion situated away from a point of attachment to the body. For example, a distal portion of a nasogastric tube can be situated away from the nose or mouth and closer to the stomach.

II. Overview

The present disclosure relates generally to measuring the depth of neuromuscular blockade. Current technologies stimulate the ulnar nerve, the facial nerve, or the posterior tibial nerve and monitor an associated twitch response. While the ulnar nerve, the facial nerve, and the posterior tibial nerve are convenient to access and observe the twitch response, the twitch response is not a reliable measure of the strength of the neuromuscular blockade. As one of the first muscles to recover from neuromuscular blockade, a twitch response of the diaphragm can provide a better reflection of the degree of the neuromuscular blockade.

The present disclosure relates, more specifically, to systems and methods for monitoring the twitch response of the diaphragm to measure the depth of neuromuscular blockade. The twitch response of the diaphragm can be monitored based on a stimulation of the phrenic nerve. The phrenic nerve has the effect of the diaphragm. A monitor device can detect the diaphragm's response to the stimulation. For example, the monitor can include a nasogastric tube with two distally positioned inflatable balloons. Each of the inflatable balloons is coupled to a sensor to measure a corresponding pressure (e.g., an esophageal pressure and a stomach (or gastric) pressure). The pressure differential between the esophagus and the stomach (or transdiaphragmatic pressure) can be used as a measure of the diaphragmatic twitch response.

III. Systems

One aspect of the present disclosure can include a system 10 (FIG. 1) that monitors a twitch response of the diaphragm to measure the depth of neuromuscular blockade. By monitoring the twitch response of the diaphragm, the system 10 can provide a more reliable measure of the depth of the neuromuscular blockade. The diaphragm is relatively resistant to neuromuscular blockade and is one of the first muscles to recover from neuromuscular blockade. Accordingly, the diaphragm begins to contract before other muscles, including peripheral muscles innervated by the ulnar nerve, the facial nerve, or the posterior tibial nerve that are monitored traditionally.

Figure 1:
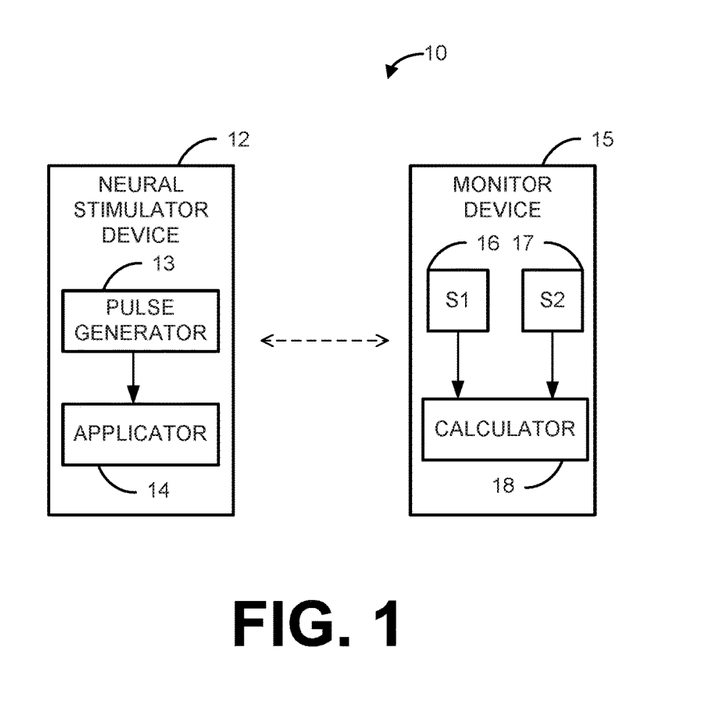
FIG. 1 is a block diagram illustration showing an example of a system that monitors a twitch response of the diaphragm to measure the depth of neuromuscular blockade in accordance with an aspect of the present disclosure.

The system 10 can provide a quantitative measure for depth of neuromuscular blockade based on neural stimulation and subsequent monitoring of the diaphragmatic response. The system 10 allows surgeries requiring neuromuscular blockade to be performed in a controlled, safe, and consistent manner without utilizing too little or too much neuromuscular blocking agent. In fact, the system 10 eliminates the guess work and cycling in and out of acceptable levels of neuromuscular blockade inherent to previous qualitative and inaccurate measures of neuromuscular blockade The system 10 can include a neural stimulator device 12 and a monitor device 15. At least a portion of the neural stimulator device 12 and at least a portion of the monitor device 15 can be coupled to one another (e.g., wired coupling, wireless coupling, and/or a combination of wired and wireless coupling) so that they work together to monitor the depth of neuromuscular blockade. For example, the neural stimulator device 12 and the monitor device 15 can use the same display device(s) and/or input device(s).

The neural stimulator device 12 can stimulate the phrenic nerve of a subject, which innervates the diaphragm. When stimulated, the phrenic nerve can signal the diaphragm to contract (or twitch). The monitor device 15 can monitor a twitch response of the diaphragm in response to the stimulation of the phrenic nerve and measure the depth of neuromuscular blockade based on the monitored twitch response. For example, the presence of a twitch and/or the strength of the twitch can be an indication of the depth of the neuromuscular blockade.

Figure 4:
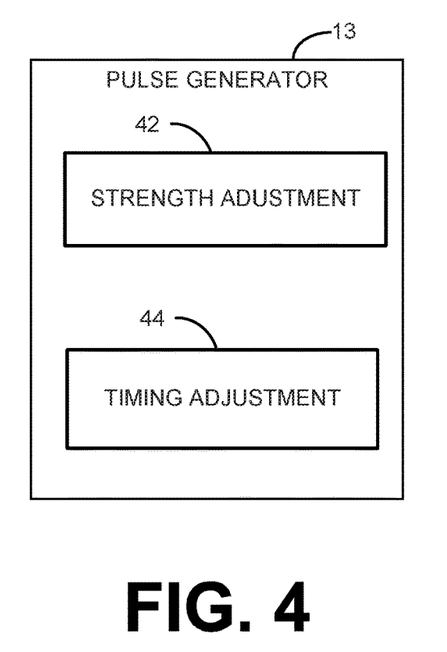
FIG. 4 is a block diagram illustration showing an example of the pulse generator of FIG. 1 in greater detail.

The neural stimulator device 12 includes a pulse generator 13 and an applicator 14. The pulse generator 13 can generate a series of pulses according to a stimulation paradigm. In some instances, at least a portion of the stimulation paradigm can be controlled by a user input (an example interface for the user input is shown in FIG. 4, with a strength adjustment 42 and a timing adjustment 44). The stimulation paradigm can include a number of pulses to apply, a timing parameter for the pulses, a period at which the number of pulses repeat, and the like.

The number of pulses set in the stimulation paradigm can be a series of one or more pulses corresponding to a "train-of-four" stimulation. In some instances, the number of pulses can include two or more pulses in succession. In other instances, the number of pulses can include three or more pulses in succession. In still other instances, the number of pulses can include four or more pulses in succession. In further instances, the number of pulses can include six or more pulses in succession. In still further instances, the number of pulses can include eight or more pulses in succession.

The timing parameters set in the stimulation paradigm can include a time that it takes for the entire series of one or more pulses to occur. For example, the time that it takes for the entire series of one or more pulses to occur be greater than 1 second. As another example, the time that it takes for the entire series of one or more pulses to occur can be more than 2 seconds.

The period at which the number of pulses repeat set in the stimulation paradigm. For example, the pulses can repeat every one minute or more. As another example, the pulses can repeat every five minutes or more. In a further example, the pulses can repeat every ten minutes or more.

In some instances, the pulse generator 13 can be a magnetic pulse generator that can create a magnetic stimulation according to the stimulation parameters. The applicator 14 can deliver a magnetic field to the subject to stimulate the phrenic nerve. In such instances, the applicator 14 can include one or more magnetic coils to deliver the magnetic stimulation to the subject. The one or more magnetic coils can be used external to the body to deliver the magnetic stimulation to the subject. For example, the one or more coils can be an external coil that can deliver transcutaneous magnetic stimulation to the subject to stimulate the phrenic nerve. The one or more magnetic coils can be placed between the C3 and C7 levels of the subject's spinal cord to stimulate the phrenic nerve. In some instances, the one or more magnetic coils can be placed at the C3-C4 level of the spinal cord. In other instances, the one or more magnetic coils can be placed at the C4-C5 level of the spinal cord. In still other instances, the one or more magnetic coils can be placed at the C6-C7 level of the spinal cord.

In other instances, the pulse generator 13 can be an electrical pulse generator that can create an electrical stimulation according to the stimulation parameters. The applicator 14 can be one or more electrodes to deliver the electrical stimulation as an electric field to the subject to stimulate the phrenic nerve. In some instances, the applicator 14 can include one or more skin electrodes and/or one or more internal electrodes. The skin electrodes can stimulate the phrenic nerve according to the stimulation parameter through the skin or another location at least partially external to the subject's body. The internal electrodes can stimulate the phrenic nerve according to the stimulation parameter from a location internal to the subject's body (e.g., via a cuff-type electrode, an electrode placed on the diaphragm near the phrenic nerve, an electrode placed within the esophagus).

When the phrenic nerve is stimulated, an electrical signal is transmitted to the diaphragm. At least a portion of the monitor device 15 detects a contraction (or twitch) of the diaphragm in response to the stimulation. When the neuromuscular blockade is in force, the diaphragm does not contract in response to the stimulus. As the neuromuscular blockade weakens, the diaphragm contracts (or twitches) in response to the stimulus. The contraction of the diaphragm can be reflected in one or more properties detected by one or more sensors (S1 16, S2 17) of the monitoring device. The one or more sensors (S1 16, S2 17) can include at least one pressure transducer, one or more electromyogram (EMG) electrodes (that can measure a compound action potential that occurs during muscular contraction), one or more accelerometer transducers, or the like. The one or more sensors (S1 16, S2 17) can be placed within the esophagus to monitor the properties related to diaphragmatic contraction based on the stimulation.

The one or more sensors (S1 16, S2 17) can communicate with a calculator 18 of the monitor device 15. The communication between the one or more sensors (S1 16, S2 17) can be via one or more wired and/or wireless connections. The calculator 18 can be stored in a non-transitory memory and executed by one or more processors of the monitor device 15. In some instances, the non-transitory memory and the one or more processors can be hardware devices. Software aspects that can be implemented by the monitor device 15 to implement at least a portion of the calculator 18 can be stored as computer program instructions in the non-transitory memory. The non-transitory memory can be any non-transitory medium that can contain or store the computer program instructions, including, but not limited to, a portable computer diskette; a random access memory; a read-only memory; an erasable programmable read-only memory (or Flash memory); and a portable compact disc read-only memory). The computer program instructions may be executed by the one or more processors. The one or more processors can be one or more processors of a general purpose computer, special purpose computer, and/or other programmable data processing apparatus. Upon execution of the computer program instructions, various functions/acts can be implemented by the monitor device 15 related to actions of the calculator 18. The calculator 18 can process the data recorded by the one or more sensors (S1 16, S2 17) to determine the presence or absence of a diaphragmatic contraction in response to the stimulation and/or an associated strength of the diaphragmatic contraction.

Additionally, the patient will need to be ventilated with a mechanical ventilator during the neuromuscular block. The mechanical ventilator can record properties, such as air flow, which will be altered if the diaphragm responds to the stimulation. The flow could increase or decrease. The recorded properties from the mechanical ventilator can also be fed in as inputs to the calculator 18.

Figure 2:
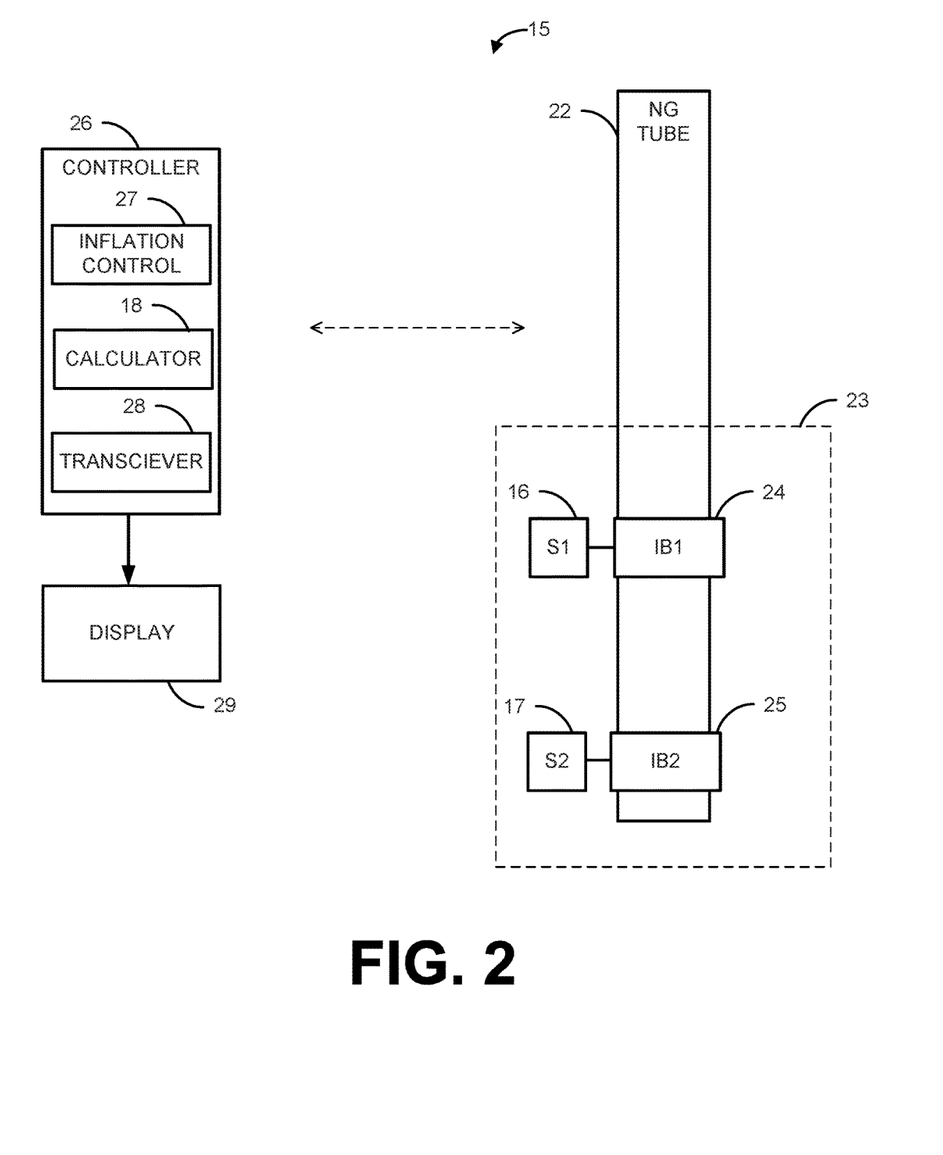
FIG. 2 is a block diagram illustration showing an example of the monitor device of FIG. 1 in greater detail.

FIG. 2 shows an example on the monitor device 15. The one or more sensors (S1 16, S2 17) can be located on or associated with device that can be inserted into the subject's nose or mouth, and run down the esophagus to the stomach. An example of such a device is a nasogastric (NG) tube 22. The one or more sensors (S1, S2 17) can be located in a distal portion 23 of the NG tube 22. In other words, the distal portion 23 can pass by the diaphragm and into the stomach. One or more inflatable balloons (IB1 24, IB2 25) can be positioned in the distal portion 23 of the NG tube 22.

The one or more sensors (S1 16, S2 17) can be associated with or connected to the one or more inflatable balloons (IB1 24, IB2 25). In some instances, the one or more sensors (S1 16, S2 17) can be embodied on the one or more inflatable balloons (IB1 24, IB2 25). For example, the one or more sensors (S1 16, S2 17) can be a bridge-type pressure sensor positioned on the one or more inflatable balloons (IB1 24, IB2 25).

The one or more inflatable balloons (IB1 24, IB2 25) can inflate to distend outwards and contact the lumen of the esophagus. For example, the inflation can be due to adding air or liquid (e.g., saline, mineral oil, or the like) to the one or more inflatable balloons (IB1 24, IB2 25). The associated sensor (S1 16 or S2 17) can measure a pressure resistance associated with the diaphragm in response to the stimulation.

The one or more sensors (S1 16, S2 17) each can be associated with an inflatable balloon (IB1 24, IB2 25) of the device, such as the NG tube 22. When the stimulation is triggered, the inflatable balloons are triggered to inflate (e.g., by the inflation control 27 of controller 26). The one or more sensors can detect a pressure associated with the inflation. The pressure recordings by the one or more sensors can provide a quantitative measurement of the status of the neuromuscular blockade. For example, when the neuromuscular blockade is in force, the diaphragm does not contract in response to the stimulus. As the neuromuscular blockade weakens, the diaphragm contracts (or twitches) in response to the stimulus.

In some examples, the NG tube 22 can include two inflatable balloons IB1 24, IB2 26) in the distal portion 23. Each of the two inflatable balloons (IB1 24, IB2 26) can be associated with a respective pressure sensor (S1 16 or S2 17). When the inflatable balloons (IB1 24, IB2 26) are inflated, the pressure sensors (S1 16 and S2 17) can each measure an associated pressure resistance. For example, one inflatable balloon (IB1 24) can be located in the distal portion 23 of the NG tube 22 within the esophagus (e.g., above the diaphragm or in line with the diaphragm), while the other inflatable balloon (IB2 25) can be located in the distal portion 23 of the NG tube 22 below the diaphragm (e.g., in or near the stomach). The first sensor (S1 16) can measure a pressure in the esophagus (near or above the diaphragm). The second sensor (S2 17) can measure a pressure, referred to as the gastric pressure, within or near the stomach (below the diaphragm). A pressure differential can be determined between the esophagus and the stomach based on the recordings of the sensors (S1 16 and S2 17). The pressure differential (referred to as the transdiaphragmatic pressure) can be a measure of the diaphragmatic twitch caused by the stimulation of the phrenic nerve, which can be used to determine the depth of the neuromuscular block.

The sensors (S1 16 and S2 17) can be coupled to a controller 26. The controller 26 can include the calculator 18, an inflation control 27, and a transceiver 28. Additionally, the controller 26 can include the non-transitory memory and the one or more processors of the monitor device 15. The controller 26 can also couple to one or more additional devices, such as a display 29 and/or a monitoring device.

For example, the inflation control 27 can receive an instruction to inflate the inflatable balloons (IB1 24, IB2 25) within the NG tube 22. The inflation control 27 can facilitate the inflation through communication with an inflation means. For example, the inflation means can be at least partially within the NG tube 22 and causes the inflatable balloons (IB1 24, IB2 25) to expand in the esophagus. Upon the expansion, the sensors (S1 16 and S2 17), which can be coupled to a controller 26 through transceiver 28 for transmission, record the associated pressure. The transceiver 28 can be a wired transceiver and/or a wireless transceiver. The sensors (S1 16 and S2 17) can transmit the recorded pressures to the controller 26 through the transceiver 28. The calculator 18 can determine the measure of the diaphragmatic twitch caused by the stimulation of the phrenic nerve, and use the measure of the diaphragmatic twitch to determine the depth of the neuromuscular blockade. In some instances, the calculator 18 can determine a pressure differential, which can be based on the recorded pressures being normalized to a baseline value or the differential can be normalized to the baseline value. Additional inputs, like from an EMG sensor or other sensors on the diaphragm or from the ventilator can affect the determination of the depth of neuromuscular blockade by the calculator 18.

Figure 3:
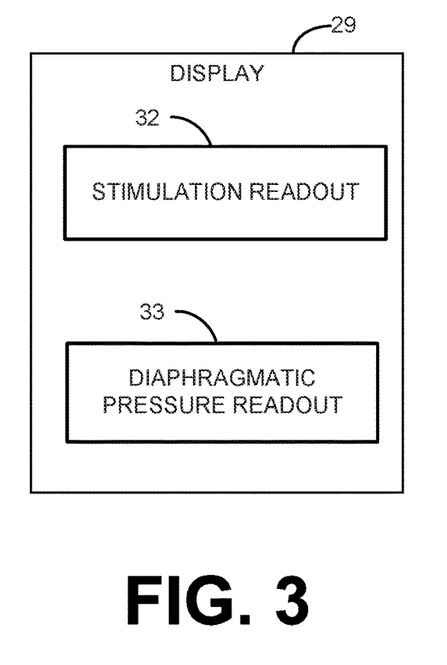
FIG. 3 is a block diagram illustration showing an example of the display of FIG. 2 in greater detail.

Properties related to the depth of neuromuscular blockade can be displayed on the display. For example, the display can be a graphical user interface that can receive inputs and/or provide outputs related to the system 10. As shown in FIG. 3, for example, the display 29 can include a neural stimulation readout 32 and an associated diaphragmatic pressure readout 33 based on the neural stimulation. The diaphragmatic pressure can be determined by the calculator 18. Additionally, the diaphragmatic pressure readout 33 can include an indication of the status of the neuromuscular blockade. The display can also include an alarm that can indicate when the neuromuscular blockade is below a certain threshold, set for the particular drug used for the neuromuscular blockade.

IV. Methods

Figure 5:
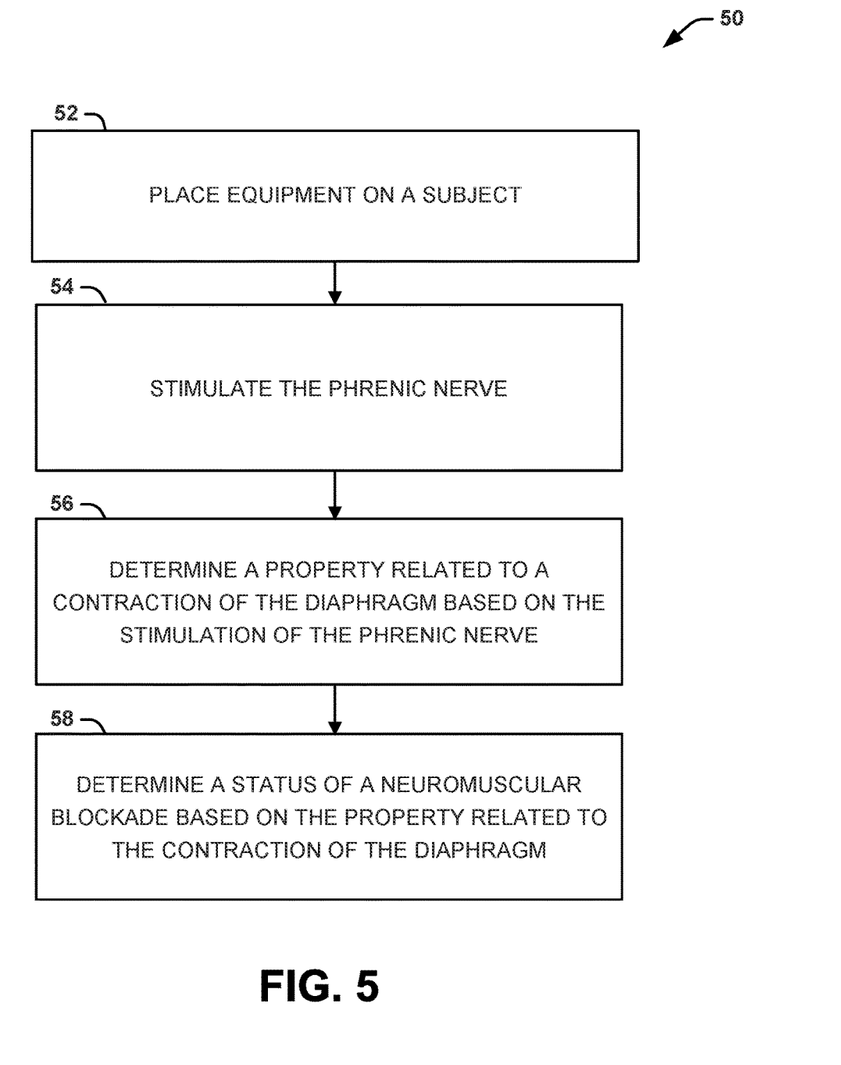
FIG. 5 is a process flow diagram of an example method for monitoring the twitch response of the diaphragm to measure the depth of neuromuscular blockade in accordance with another aspect of the present disclosure.

As shown in FIG. 5, another aspect of the present disclosure can include a method 50 for monitoring the twitch response of the diaphragm to measure the depth of neuromuscular blockade. The method 50 is illustrated as process flow diagrams with flowchart illustrations. For purposes of simplicity, the method 50 is shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the method 50. The method 50 can be executed by hardware—for example, at least a portion of the system 10 shown in FIG. 1. One or more hardware elements, such as controller 26, pulse generator 13, and/or display 29, can execute software routines to implement at least a portion of the method 50. Additionally, one or more of the controller 26, pulse generator 13, and/or display 29, can include a non-transitory memory storing the software routines and one or more processors to execute the software routines corresponding to the at least the portion of the method 50.

At 52, equipment can be placed on a subject. The equipment can include a neural stimulation device (e.g., neural stimulator device 12) and a monitoring device (e.g., monitor device 15). The monitoring device can include one or more sensors (e.g., S1 16, S2 17, or the like), including at least one pressure sensor. Other types of sensors that can be part of the one or more sensors can include one or more electromyogram (EMG) electrodes, one or more acceleromyogram transducers, or the like. In some instances, the one or more sensors each can be associated with one or more inflatable balloons (e.g., IB1 24 and IB2 25). The inflatable balloons can be associated with a portion (e.g., distal portion 23) of a device (e.g., NG tube 22) that can be inserted into the subject's nose or mouth, through the subject's esophagus, and into the subject's stomach.

At least a portion of the equipment can be placed on the subject preoperatively. For example, the neural stimulation electrodes or coils can be placed on the subject preoperatively, while the pulse generator may be placed on or connected t the subject preoperatively or during the operation. Similarly, the device, e.g., the NG tube, of the monitoring device can be placed on the subject preoperatively, while the controller and/or display of the monitoring device can be placed on or connected to the subject preoperatively or during the operation.

At 54, the neural stimulation device can deliver a stimulation to the phrenic nerve of the subject. The stimulation can be delivered according to a stimulation paradigm. The stimulation paradigm can include a series of one or more pulses corresponding to a "train-of-four" stimulation. In some instances, the stimulation paradigm can include two or more pulses in succession. In other instances, the stimulation paradigm can include three or more pulses in succession. In still other instances, the stimulation paradigm can include four or more pulses in succession. In further instances, the stimulation paradigm can include six or more pulses in succession. In still further instances, the stimulation paradigm can include eight or more pulses in succession. The stimulation paradigm can provide the number of pulses in a time period. The stimulation paradigm can also include one or more timing parameters. For example, the timing parameter can include a time period greater than 1 second. As another example, the timing parameter can include a time period be more than 2 seconds. In some instances, the time period can also include a period when the series of pulses repeats.

In some instances, the stimulation delivered to the phrenic nerve can be a magnetic stimulation, in which a magnetic field is delivered to the subject to stimulate the phrenic nerve. The neural stimulation device delivering magnetic stimulation can include one or more coils that are used external to the body to deliver the magnetic stimulation according to the stimulation paradigm. For example, the one or more coils can be an external coil that can deliver transcutaneous magnetic stimulation to the subject to stimulate the phrenic nerve.

In other instances, the stimulation delivered to the phrenic nerve can be an electrical stimulation, in which an electric field is delivered to the subject to stimulate the phrenic nerve. The neural stimulation device delivering electrical stimulation can include one or more skin electrodes and/or one or more internal electrodes. The skin electrodes can stimulate the phrenic nerve according to the stimulation parameter through the skin or another location at least partially external to the subject's body. The internal electrodes can stimulate the phrenic nerve according to the stimulation parameter from a location internal to the subject's body (e.g., via a cuff-type electrode, an electrode placed on the diaphragm near the phrenic nerve, an electrode placed within the esophagus).

As an example, an anesthesiologist can trigger neural stimulation to learn a status of a neural blockade in the subject during the surgical procedure. The stimulation of the phrenic nerve (either magnetic or electrical) causes an electrical signal to be transmitted to the diaphragm. For example, when the neuromuscular blockade is in force, the diaphragm does not contract in response to the stimulus. As the neuromuscular blockade weakens, the diaphragm contracts (or twitches) in response to the stimulus. The contraction of the diaphragm can be reflected in the pressure detected by the one or more sensors. The one or more sensors each can be associated with an inflatable balloon of the device, such as the NG tube. When the stimulation is triggered, the inflatable balloons are triggered to inflate (e.g., by the inflation control 27 of controller 26). The one or more sensors can detect a pressure associated with the inflation. The pressure recordings by the one or more sensors can provide a quantitative measurement of the status of the neuromuscular blockade.

For example, at 56, a property related to a contraction of the diaphragm can be determined (e.g., by calculator 18 of controller 26) based on the stimulation of the phrenic nerve. For example, the property related to the contraction can be a pressure measured within the esophagus by at least one of the sensors. The one or more pressure sensors can measure a pressure within the esophagus above the diaphragm or stomach below the diaphragm due to an inflation of the respective inflatable balloons. When the diaphragm contracts, the pressure within the esophagus will be greater than the pressure within the esophagus without contraction. In some instances, one sensor associated with an inflatable balloon near the diaphragm can record an esophageal pressure and another sensor associated with another inflatable balloon near or within the stomach can record a stomach (or gastric) pressure. In this case, a differential pressure (also referred to as the transdiaphragmatic pressure) can be determined based on the recording from the first sensor and the second senor. The differential recording can be normalized to a baseline value for comparison purposes.

At 58, a status of the neuromuscular blockade can be determined (e.g., by calculator 18 of controller 26) based on the property related to the contraction of the diaphragm. The status of the neuromuscular blockade can be discrete or continuous. For example, if the property related to the contraction of the diaphragm indicates no contraction, the status of the neuromuscular blockade is acceptable. However, if the property related to the contraction of the diaphragm indicates that the diaphragm has contracted (or twitched) in response to the stimulation, the status of the neuromuscular blockade is beginning to recover and more neuromuscular blocking agent should be administered. In some instances, a threshold for acceptable levels of diaphragm contraction can be established based on the neuromuscular blocking agent used. The status can be displayed (e.g., on display device 29) for use by the anesthesiologist. Based on the displayed status, the anesthesiologist can take further action related to the neuromuscular blockade.

From the above description, those skilled in the art will perceive improvements, changes and modifications. Such improvements, changes and modifications are within the skill of one in the art and are intended to be covered by the appended claims.

What is claimed is:

1. A system comprising:
a neural stimulation device to stimulate a phrenic nerve of a subject; and
a nasogastric tube comprising:
an inflatable balloon positioned in a distal portion of the nasogastric tube;
a sensor connected to the inflatable balloon to measure a pressure in an esophagus of the subject when the inflatable balloons is inflated;
another inflatable balloon positioned in the distal portion of the nasogastric tube; and
another sensor connected to the other inflatable balloon to measure a pressure in a stomach of the subject when the other inflatable balloon is inflated,
wherein the pressure differential between the esophagus of the subject and the stomach of the subject is a measure of diaphragmatic twitch based on the stimulation of the phrenic nerve.

2. The system of claim 1, further comprising a controller to determine the pressure differential and normalize the pressure differential to a baseline value.

3. The system of claim 1, wherein the neural stimulation device comprises:
a magnetic stimulator; and
at least one magnetic coil to deliver a magnetic field to the subject for transcutaneous magnetic stimulation of the phrenic nerve of the subject.

4. The system of claim 1, wherein the neural stimulation device comprises:
an electric stimulator; and
at least one skin electrode or implanted electrode to deliver an electric current to the subject to stimulate the phrenic nerve of the subject.

5. The system of claim 1, wherein the neural stimulation device comprises:
an electric stimulator; and
at least one electrode located on the inflatable balloon to deliver an electric current to the subject to stimulate the phrenic nerve of the subject.

6. The system of claim 1, wherein the nasogastric tube is coupled to a pressure monitor device,
wherein the pressure monitor device provides an output related to the pressure differential.

7. The system of claim 6, wherein the pressure monitor device is coupled to at least a portion of the neural stimulation device to provide an output related to the stimulation.

8. The system of claim 6, wherein the pressure monitor device is configured to provide an alarm when the detected pressure is above a threshold.

9. The system of claim 6, wherein the pressure monitor is configured to provide the detected pressure to a graphical user interface for display.

10. The system of claim 1, wherein the nasogastric tube further comprises a mechanism to inflate the inflatable balloons.

11. The system of claim 1, further comprising a mechanical ventilator to provide ventilation to the subject during the neuromuscular blockade.

12. The system of claim 1, wherein at least one of the sensors comprises an electrode configured to monitor a resulting action potential of the diaphragm when the phrenic nerve is stimulated.

13. A method comprising:
placing equipment on a subject pre-operatively, wherein the equipment comprises a neural stimulation device and a monitoring device, wherein the monitoring device comprises two inflatable balloons positioned in a distal portion of a nasogastric tube; and a sensor associated with each inflatable balloon;
stimulating, by the neural stimulation device, the phrenic nerve of the subject with a series of pulses;
determining, by the monitoring device, a pressure differential between the esophagus of the subject and the stomach of the subject based on recordings by the sensors upon inflation of the inflatable balloons; and
determining a status of a neuromuscular blockade based on the pressure recorded,
wherein the pressure differential corresponds to a twitch response of the subject's diaphragm based on the series of pulses stimulating the phrenic nerve.

14. The method of claim 13, wherein the series of pulses corresponds to a train-of-four stimulation.

15. The method of claim 14, wherein the train-of-four simulation comprises:
stimulating the phrenic nerve at least four times over at least two seconds; and
recording the pressure differential between the esophagus and the stomach corresponding to each stimulation of the phrenic nerve.

16. The method of claim 13, wherein the recordings by the sensors provide a quantitative measurement of the status of the neuromuscular blockade.

17. The method of claim 13, wherein the stimulating comprises delivering a magnetic field to the subject by an external coil for transcutaneous magnetic stimulation of the phrenic nerve of the subject, wherein the neural stimulation device comprises the external coil.

18. The method of claim 13, wherein the stimulating comprises delivering an electric current to the subject via a skin electrode to stimulate the phrenic nerve of the subject, wherein the neural stimulation device comprises the skin electrode.

19. The method of claim 13, wherein the stimulating comprises delivering an electric current to the subject via an internal electrode to stimulate the phrenic nerve of the subject, wherein the neural stimulation device comprises the internal electrode.

* * * * *